US009788567B2

(12) United States Patent
Abe et al.

(10) Patent No.: US 9,788,567 B2
(45) Date of Patent: Oct. 17, 2017

(54) ERGOTHIONEINE-CONTAINING HEN¿ S EGG AND METHOD OF PREPARING HEN¿ S FEED FOR PRODUCING SAME

(71) Applicants: Origin Biotechnology Kabushikikaisha, Nagano-ken (JP); KABUSHIKIKAISHA HOKKEN, Tochigi-ken (JP)

(72) Inventors: Kazunari Abe, Nagano-ken (JP); Toshiaki Ohshima, Tokyo (JP); Rikuo Fukui, Tochigi-ken (JP)

(73) Assignees: ORIGIN BIOTECHNOLOGY KABUSHIKIKAISHA, Nagano-Ken (JP); KABUSHIKIKAISHA HOKKEN, Tochigi-Ken (JP)

( * ) Notice: Subject to any disclaimer, the term of this patent is extended or adjusted under 35 U.S.C. 154(b) by 0 days.

(21) Appl. No.: 15/108,095

(22) PCT Filed: Nov. 20, 2014

(86) PCT No.: PCT/JP2014/080738
§ 371 (c)(1),
(2) Date: Jun. 24, 2016

(87) PCT Pub. No.: WO2015/098380
PCT Pub. Date: Jul. 2, 2015

(65) Prior Publication Data
US 2016/0324199 A1   Nov. 10, 2016

(30) Foreign Application Priority Data

Dec. 27, 2013   (JP) .................................. 2013-272754

(51) Int. Cl.
*A23L 15/00*   (2016.01)
*A23K 50/75*   (2016.01)
(Continued)

(52) U.S. Cl.
CPC .............. *A23L 15/30* (2016.08); *A23K 10/12* (2016.05); *A23K 10/30* (2016.05); *A23K 20/142* (2016.05);
(Continued)

(58) Field of Classification Search
CPC ........ A23L 15/00; A23L 15/30; A23L 33/175; A61Q 19/00; A61K 8/4946; A61K 8/982;
(Continued)

(56) References Cited

U.S. PATENT DOCUMENTS

| 5,733,539 A | 3/1998 | Kitano |
| 2005/0084500 A1* | 4/2005 | Molly .................. A61K 36/068 424/195.15 |

FOREIGN PATENT DOCUMENTS

| JP | 5-153935 | * | 6/1993 |
| JP | H09-121783 A | | 5/1997 |

(Continued)

OTHER PUBLICATIONS

Derwent Abstract for JP2009-278895 published Dec. 2009.*
(Continued)

*Primary Examiner* — Anthony Weier
(74) *Attorney, Agent, or Firm* — Pearne & Gordon LLP

(57) ABSTRACT

To provide a production technique for an edible egg that contains a sufficient amount of ergothioneine by using the biological accumulation of the ergothioneine in eggs, and that has antioxidative activity. This ergothioneine-containing egg is obtained from a hen raised by being fed a hen feed for a prescribed time period, the hen feed being manufactured by manufacturing the ergothioneine-containing extract solution from a waste medium used in the production of edible mushrooms and mixing a prescribed amount of the extract solution into a feed for the hen used generally.

3 Claims, 4 Drawing Sheets

(51) Int. Cl.
|  |  |
| --- | --- |
| *A61Q 19/00* | (2006.01) |
| *A61K 8/49* | (2006.01) |
| *A61K 8/98* | (2006.01) |
| *A23K 10/12* | (2016.01) |
| *A23K 10/30* | (2016.01) |
| *A23K 20/168* | (2016.01) |
| *A23K 20/142* | (2016.01) |
| *A23L 33/175* | (2016.01) |

(52) U.S. Cl.
CPC .......... *A23K 20/168* (2016.05); *A23K 50/75* (2016.05); *A23L 15/00* (2016.08); *A23L 33/175* (2016.08); *A61K 8/4946* (2013.01); *A61K 8/982* (2013.01); *A61Q 19/00* (2013.01); *A23V 2002/00* (2013.01)

(58) Field of Classification Search
CPC ...... A23K 10/12; A23K 10/30; A23K 20/168; A23K 20/142; A23K 50/75
See application file for complete search history.

(56) References Cited

FOREIGN PATENT DOCUMENTS

| | | | |
|---|---|---|---|
| JP | 2008-148717 | A | 7/2008 |
| JP | 2009-201472 | A | 9/2009 |
| JP | 2009-219377 | A | 10/2009 |
| JP | 2009-278895 | * | 12/2009 |
| JP | 2012-019774 | A | 2/2012 |
| JP | 5088911 | B2 | 12/2012 |
| JP | 2014-223051 | A | 12/2014 |
| KR | 20030081814 | * | 10/2003 |
| KR | 960892 | * | 6/2010 |
| KR | 20120051879 | * | 5/2012 |
| KR | 101187564 | * | 10/2012 |
| KR | 20120138079 | * | 12/2012 |

OTHER PUBLICATIONS

English Abstract for KR960892 published Jun. 2010.*
English Abstract for KR20120051879 published May 2012.*
English Abstract for KR20120138079 published Dec. 2012.*
English Abstract for JP5-153935 published Jun. 1993.*
English Abstract for KR20030081814 published Oct. 2003.*
English Translation for KR101187564 published Oct. 2012.*
Derwent Abstract for CN102273544 published Dec. 2011.*
Derwent Abstract for KR 960892 published Jun. 2010.*
Derwent Abstract for CN 201210011783 published Jul. 2012.*
English Abstract for CN102894230 pbulished Dec. 2013.*
Derwent Abstract for KR2007016311 published Feb. 2007.*
Derwent Abstract for CN101214048 published Jul. 2008.*
Derwent Abstract for CN103125737 published Jun. 2013.*
Derwent Abstract for CN103027196 published Apr. 2013.*
Willis et al. Poultry Science. 2007. vol. 86. pp. 1856-1860.*
Zhang et al. Short Communication. Bioresource Technology 52. 1995. pp. 89-91.*
Willis et al. Journal of Applied Poultry Res. 2008. vol. 18. pp. 658-664.*
Cheong et al. Korean Journal of Mycology. 2006. vol. 34. No. 1. pp. 29-33.*
English Translation for JP2012180329 published Dec. 2012.*
English Translation for JP5088911 published Dec. 2012.*
English Translation for Cheong et al. 2006. vol. 34, No. 1. pp. 29-33.*
International Search Report issued in Application No. PCT/JP2014/080738 dated Feb. 24, 2015 .
Suggestion material of advanced technology, "The business which develops a high technique for revival in a food production area", Suggestion meeting of a high technique (Fields of Agriculture and Rural community) (The 1st time), dated Jan. 6, 2013, retrieved Feb. 10, 2015.
Summary of Proceedings, "The business which develops a high technique for revival in a food production area", Suggestion meeting of a high technique (Fields of Agriculture and Rural community) (The 1st time), dated Feb. 4, 2013, retrieved Feb. 10, 2015.

* cited by examiner

ERGOTHIONEINE-CONTAINING HEN¿ S EGG AND METHOD OF PREPARING HEN¿ S FEED FOR PRODUCING SAME

TECHNICAL FIELD

The present invention relates to a technology for producing an edible hen's egg containing ergothioneine of a high concentration, by using a waste culture medium that was used for an edible mushroom production to manufacture a feed of a laying hen, by laying the egg in the laying hen raised by feeding the feed.

BACKGROUND ART

It is widely known that the ergothioneine has a high antioxidant action and exhibits functions such as aging prevention by taking the ergothioneine in a human body. It is known that the laying hen which gave and raised the feed which blended various components will lay the hen's egg which exerts characteristic efficacy.

About the feed and the raising method of the hen, and the hen's egg obtained by them, Patent reference 1 discloses the feed of the laying hen that lays the egg containing DHA component, the feeding method for giving and feeding the feed to the hen and the hen's egg containing the DHA component. In the Patent reference 1, the feed is added a mixture obtained by mixing 5-200 copies of oils produced by extracting a seed of a perilla and a strained lees of the perilla, the total amount of the mixed feed is 1000 copies. The Patent reference 1 is intended to obtain the hen's egg containing the DHA component by paying attention to the point that the DHA lowers a serum cholesterol value, the DHA is to reduce the onset of diseases of the cardiovascular system, to promote the development of brain and nerve tissue. The DHA which is useful material is made to contain in the hen's egg here.

Patent reference 2 discloses the feed for the hen containing a palm oil for obtaining the hen's egg for a cake or bread dough creation. In the Patent reference 2, the feed contains the palm oil for including 0.1-0.2 part by weight of palm oil components, for 100 parts by weight of materials which comprise a corn component, a protein component which comprises fish meal, soybean meal and corn gluten, a fat and oil component which comprises lard and soybean oil, a calcium component which comprises calcium carbonate and an oystershell, a phosphorus component of calcium phosphate, a vitamin, and a mineral. The Patent reference 2 is intended to obtain the hen's egg having the unique character, like the protein of an egg white is rich in foamability by feeding the hen to the feed. Here, as for creating the bread and cake rises baked softly, the inclusion of the palm oil component in eggs. Although it is known widely that excessive active oxygen of human being's inside of the body will have an adverse effect on a human body in recent years, the egg in the Patent references 1 and 2 mentioned above do not include an antioxidant.

In the feed for the fish which contains a Flammulina velutipes extract, a culture method of the fish and the fish cultivated by the culture method, Patent reference 3 discloses the feed for the fish containing the Flammulina velutipes extract, the culture method, and the fish cultivated by the culture method or its processed goods. This invention is intended to obtain the culture method and the feed for the fish which can obtain the fish to which discoloration of the color of fish meat, especially the color of dark-flesh does not take place easily at the time of circulation or preservation without processing fresh fish meat. The food for the fish in this invention uses the Flammulina velutipes extract. Here, although the discoloration prevention effect of the fish meat had been acquired by adding the Flammulina velutipes extract in the feed of the fish, since there were few antioxidants of the Flammulina velutipes origin included in the fish meat, many antioxidants were not able to be taken in for the fish meat on a human body as edible. Since many components which are not suitable for edible with the ergothioneine are contained in the waste culture medium after the production of the edible mushroom, the ergothioneine for edible was not able to be generated from the waste culture medium after the production of the edible mushroom.

PRIOR ART REFERENCE

Patent Reference

Patent reference 1: Jpn. Pat. Appln. KOKAI Publication No. 2009-201472
Patent reference 2: Jpn. Pat. Appln. KOKAI Publication No. 2008-148717
Patent reference 3: Jpn. Pat. Appln. KOKAI Publication No. 2009-219377

SUMMARY OF INVENTION

Problem to be Solved by Invention

The problem given to the present invention is providing the manufacturing technique of the edible hen's egg which has the antioxidative activity and which contains the ergothioneine sufficiently using the biological concentration to the hen's egg of the ergothioneine.

Means for Solving Problem

Inventors know that to be efficiently extractable the ergothioneine from the edible mushroom such as the Flammulina velutipes, have been considered about use of the abandonment culture medium used for production for the edible mushroom which was conventionally troubled by abandonment. Under such a situation, the inventors mix the extract solution extracted from the abandonment culture medium used for the production of the Flammulina velutipes to the feed for the hen used generally, give the feed to the laying hen and raise, analyze about the component of the egg which the hen laid, find out that the ergothioneine is efficiently concentrated and accumulated to the egg and many ergothioneine is contained in the egg white and the egg yolk. Research of the technology of producing the edible hen's egg which contains the ergothioneine is repeated by applying the principle of a biological concentration, and the present invention is attained. In the present invention, as the edible mushroom, the Flammulina velutipes, the *Pleurotus eryngii*, the *Lentinula edodes*, the *Pleurotus cornucopiae* var. citirinopoileatus, the *Hypsizigus marmoreus*, the *Coprinus comatus*, etc. are mentioned.

The invention according to claim 1 is a manufacture method of a feed for a laying hen containing ergothioneine comprising adding water, hot water, or steam to a waste culture medium used for an edible mushroom production and heating the waste culture medium, performing a hot water extract for 30 to 90 minutes after reaching 50° C. to 110° C. to obtain an extract, separating a solid as residue from the extracted extract by a compression processing to obtain an extract solution, separating and removing moisture from the extract solution to obtain the extract solution containing the ergothioneine which is concentrated to 1/10 to 1/30, and mixing the extract solution containing the ergothioneine of 4 to 20% by weight ratio to a compound feed. In the invention according to claim 2, the edible mushroom is selected from a Flammulina velutipes, a *Pleurotus eryngii* and a *Lentinula edodes*. In the invention, the waste culture medium used for the production of a *Lentinula edodes*, a *Pleurotus cornucopiae* var. citirinopoileatus, a *Hypsizigus marmoreus*, a *Coprinus comatus* as the waste culture medium can be used.

In the extract solution containing the ergothioneine of the present invention, an alcohol solution which has ethanol of 60 to 80% (preferably about 70%) and water of 40 to 20% (preferably about 30%) are added to the waste culture medium, and the alcohol solution heats, and after reaching 40° C. to 60° C. (preferably about 50° C.), an extraction can be performed for 80 to 100 minutes (preferably about 90 minutes), the extract solution is obtained by a compression processing to separate a solid as residue from the extracted extract. In the present invention, the extract pressed out without heating and obtained by adding water to the waste culture medium used for the edible mushroom production is also applicable. In the present invention, the residue separated the extract solution by the compression processing from the extract which extracts from the alcohol solution or the hot water is reused as the waste culture medium for the mushroom production.

In the present invention, the extract solution containing the ergothioneine is added 10 to 40% (preferably about 20 to 30%) by weight ratio for a brown rice or a brown rice mixed a ground shell, is heated, and is maintained at 70 to 90° C. (preferably about 80° C.), a fermentation processing is carried out for 44 to 52 hours (preferably about 48 hours), and the extract solution is obtained by condensing to 1/10 to 1/30 (preferably about 1/20) to remove moisture. The extract solution containing the ergothioneine is mixed 4 to 20% (preferably about 10 to 13%) by weight ratio for a feed of the laying hen used generally.

In the present invention, the feed of 60 to 180 g (preferably about 100 to 140 g, more preferably about 120 g) per a hen feeds once or dividing into two to six times a day and continuously feeds from 10 days to 30 days. It is possible to lay the hen's egg containing the ergothioneine in the laying hen in this way. The egg has a boiled egg and a fried egg processed, etc.

The invention according to claim 3 is a hen's egg comprising an egg white containing ergothioneine 5 to 13 µg/g, and an egg yolk containing ergothioneine 3 to 13 µg/g, and a radical scavenging ability per unit weight of the ergothioneine contained in the egg white is 1.4 or more times a radical scavenging ability per unit weight of the ergothioneine contained in the egg yolk. In the present invention, the processed food of the egg white has a supplement, a fish paste, cosmetics, and drugs in which the egg white as a raw material. The processed food of the egg yolk has mayonnaise sauce in which the egg yolk as a raw material.

Effect of Invention

In the present invention, the extract solution containing the ergothioneine manufactured from the waste culture medium which became unnecessary after using for the production of the edible mushroom specified quantity mix to the feed for the hen used generally, this feed is referred to as the feed for the laying hen. The ergothioneine incorporated into the inside of the body of the laying hen which fed the feed is condensed and accumulated in order of the egg yolk from the egg white, the progress of the increase of the ergothioneine content in the egg white and the egg yolk of the egg which the hen after feeding for a fixed time laid stops and the ergothioneine content stabilizes at high concentration. The ergothioneine-containing hen's egg in high concentration is obtained at this time, especially the hen's egg of the egg white having the high antioxidative activity can be produced.

the concentrate solution containing the ergothioneine is obtained by condensing the extract solution mixed in the feed of the laying hen used generally to predetermined concentration by the thin film condensation processing and the brown rice fermentation processing, as a result, the feed can be adjusted to the moisture percentage which the hen likes, and the laying hen can be made to take in the feed which contained the ergothioneine efficiently.

Since the manufacture of the feed for the laying hen according to the present invention uses the waste culture medium used for the production of the edible mushroom, the hen's egg having the high antioxidative activity can produce inexpensive. The residue after separating the extract solution containing the ergothioneine from the extract containing the ergothioneine obtained by the hot water extract is recyclable as the culture medium for the production of the mushroom. The effective use of the waste culture medium used for production of the edible mushroom which was conventionally troubled by abandonment is enabled.

MODES FOR CARRYING OUT INVENTION

Figure 1:
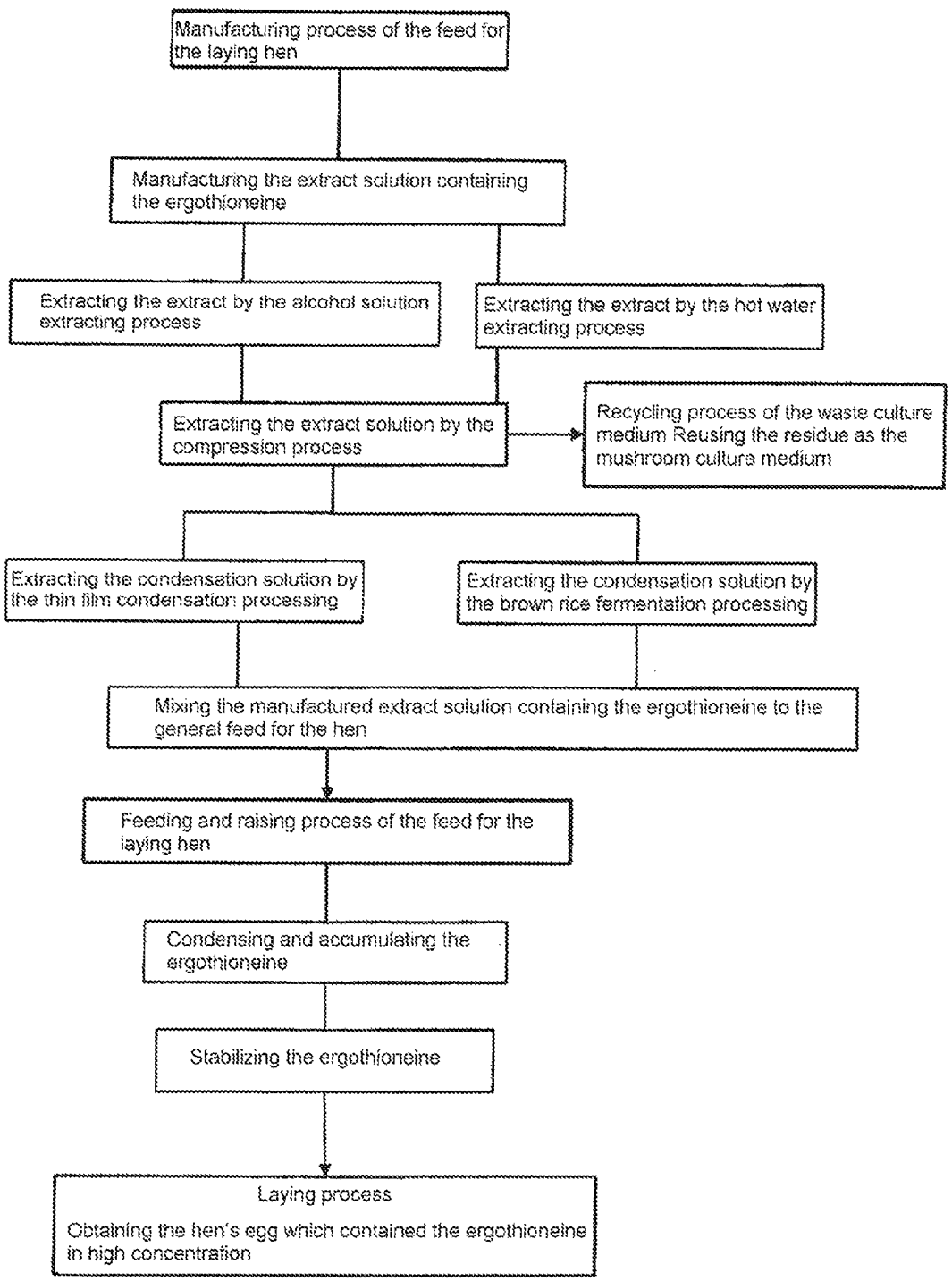
FIG. 1 It is a flow chart for describing a process until it obtains the hen's egg which the laying hen laid from manufacture of the feed for the laying hen which contains the extract solution containing the ergothioneine according to the present invention.

Hereinafter, referring to an attached drawing, it describes about the embodiment of the ergothioneine-containing egg and feeding and raising method and feed for laying hen that lays the ergothioneine-containing egg according to the present invention. FIG. 1 is a flow chart which describes the production process of the functional hen's egg which contains the ergothioneine in high concentration according to the present invention. As shown in FIG. 1, the production method of the ergothioneine-containing egg in the present invention comprises manufacturing the extract solution containing the ergothioneine from the abandonment culture medium (henceforth a "waste culture medium") which became unnecessary after using for production of the edible mushroom, manufacturing the feed for the hen in the present invention (only henceforth "the feed for the laying hen") by specified quantity mixing the manufactured extract solution to the feed for the hen used generally (only henceforth "the general feed for the hen") (manufacturing process of the feed for the laying hen), feeding and raising the manufactured feed for the laying hen to the laying hen for prescribed period (feeding and raising process), obtaining the ergothioneine-containing egg from the raised hen (raising process).

In the manufacturing process of the extract solution containing the ergothioneine, the residue separated the extract solution containing the ergothioneine from the extract containing the ergothioneine which extracts from the alcohol solution or the hot water is reused as the waste culture medium for the mushroom production (waste culture medium recycling process). In the feeding and raising process, the ergothioneine incorporated into the inside of the body of the hen is condensed and accumulated in order of the egg yolk from the egg white of the egg (ergothioneine concentration and accumulation), after feeding for a fixed time, the progress of the increase of the ergothioneine content in the egg white and the egg yolk stops and the ergothioneine content stabilizes at high concentration (ergothioneine stabilization). The ergothioneine-containing egg in high concentration is obtained from the raised hen at this time (raising process).

In the manufacturing process of the extract solution containing the ergothioneine, the alcohol solution extracting process and the hot water extracting process are adopted as a processing method which extracts the extract solution containing the ergothioneine in the present invention. In the alcohol solution extracting process, the alcohol solution which has the ethanol of 60 to 80% (preferably about 70%) and the water of 40 to 20% (preferably about 30%) are added to the waste culture medium used for the production of the edible mushroom, and the alcohol solution heats, and the extraction can be performed for 80 to 100 minutes (preferably about 90 minutes) under the temperature of 40° C. to 60° C. (preferably about 50° C.). The extract solution containing the ergothioneine is obtained by the compression processing to separate the solid as residue from the extracted extract. Although most alcohol content transpires from the extract solution in the alcohol solution extracting process and the compression process stage mentioned below, in the case of remaining the alcohol moiety in the extract solution, distillation and collection process of the alcohol moiety is carried out in addition to the compression process. The extract solution containing the ergothioneine which was prepared by the fixed moisture content can also be obtained without the compression process by the transpiration of alcohol moiety.

In the hot water extracting process, the water, the hot water, or the steam is added to the waste culture medium and the waste culture medium is heated, and the hot water extract is performed for 30 to 90 minutes (preferably about 60 minutes) after reaching 50° C. to 110° C. (preferably about 70° C. to 90° C.) to extract the extract. The extract solution containing the ergothioneine is obtained by the compression processing to separate the solid as residue from the extracted extract. In the hot water extracting process, the hot water extract can also be performed by adding the hot water or the steam to the waste culture medium instead of the water. Although the waste culture medium used by the alcohol solution extracting process and the hot water extracting process is preferably used for either the production of the *Flammulina velutipes* or the *Pleurotus eryngii*, the waste culture medium used for the production of the edible mushroom such as the *Lentinula edodes*, the *Pleurotus cornucopiae* var. citirinopoileatus, the *Hypsizigus marmoreus* as the waste culture medium can also be used effectively. In the present invention, the extract or the extract solution pressed out without heating and obtained by adding water to the waste culture medium used for the production of the edible mushroom, and heating is also applicable.

The compression process separates residue for the extract extracted by the alcohol solution extracting process or the hot water extracting process, and the extract solution containing the ergothioneine is obtained (compression process). The thin film condensation processing and the brown rice fermentation processing are adopted as the condensation processing method of adjusting the moisture content of the extract containing the ergothioneine obtained by compressing in the present invention. In the thin film condensation processing, the condensation solution containing the ergothioneine is obtained by condensing to $1/10$ to $1/30$ (preferably about $1/20$) to separate and remove the moisture from the extract solution obtained by the compression processing from the extract which extracts from the alcohol solution or the hot water.

In the brown rice fermentation processing, about 300 liters of the extract solution obtained by the compression processing from the extract which extracts from the alcohol solution or the hot water is added for 1 to 1.5 t of the brown rice or the brown rice mixed the ground shell, is heated, and is maintained at 70 to 90° C. (preferably about 80° C.), the fermentation processing is carried out for 44 to 52 hours (preferably about 48 hours), and the condensation solution containing the ergothioneine is obtained by condensing to $1/10$ to $1/30$ (preferably about $1/20$) to remove moisture. The moisture is absorbed into the brown rice by fermentation, and the moisture evaporates by the high temperature of about 80° C., and it is prepared by the fixed moisture content. Although an oystershell is suitable as the shell mixed in the brown rice here, the shellfish is not limited to this, ground finely various shells, such as a freshwater clam and an asari clam, can be used.

In the compression processing, the residue separated the extract solution containing the ergothioneine from the extract is reused as the waste culture medium for the mushroom production (waste culture medium recycling process). The substance which inhibits growth of mushrooms, enzymes such as RNase and amine degrading enzyme and polymers derived from the living body is accumulated in the abandonment culture medium used for the production of the edible mushroom. In order for some of waste to move to the extract solution containing the ergothioneine at the time of extraction of the extract in the hot water extracting process, the substance content that inhibits the growth of the mushroom in the residue is reduced after the extract solution the compression process was separated. Therefore, it becomes possible to use again the residue from which the extract was separated as the culture medium for the production of the mushroom. Jpn. Pat. Appln. KOKAI Publication No. 2011-83206 discloses that the method of reproducing a waste mushroom culture medium as a new bacteria bed. In Jpn. Pat. Appln. KOKAI Publication No. 2011-83206, a hazardous substance decomposes from the waste mushroom culture medium, it extracts, removes and sterilizes, the substance that inhibits the growth of the mushroom is inactive and dry suitably by passing steam to the abandonment culture medium once used for mushroom production.

The feed for the hen manufactures by specified quantity mixing the extract solution containing the ergothioneine extracted by the compression processing or the condensation solution containing the ergothioneine extracted by the brown rice fermentation processing to the feed for the hen used generally (the general feed for the hen). Although the feed for hen used generally is also called a compound feed, and is a powdery part which uses corn, soybean cake, oil cake, fish meal, etc. as a raw material, the general feed for the hen used in the present invention is not limited to this, and the feed containing various raw materials or the feed used by an ordinary home can be used. Although based also on the kind of the general feed for the hen, the extract solution containing the ergothioneine or the condensation solution containing the ergothioneine is mixed 4 to 20% (preferably about 10 to 13%) by weight ratio for the general feed for the hen. The hen can like the to some extent high feed of moisture percentage, and it can be adjusted to the feed of the moisture percentage which the hen likes by carrying out specified quantity addition mixing of the extract solution which is a liquefied object in the present invention.

Although the feed obtained by specified quantity mixing the extract solution containing the ergothioneine extracted by the compression process with the general feed for the hen here can also be used as the feed for laying hen, the concentrate solution containing the ergothioneine which condensed the extract solution mixed in the general feed for the hen by the thin film condensation processing and the brown rice fermentation processing to predetermined concentration, for example, $1/10$ to $1/30$, preferably about $1/20$ in the general feed for the hen, mixes with the general feed for the hen, as a result, the feed can be adjusted to the moisture percentage which the hen likes, and the laying hen can be made to take in the feed which contained the ergothioneine efficiently.

The extract solution containing the ergothioneine obtained by condensing to about $1/20$ by the compression processing or the condensation solution obtained by the thin film condensation processing or the brown rice fermentation processing is mixed 4 to 20% (preferably about 10 to 13%) by weight ratio for the feed of the laying hen used generally (the general feed for the hen). Feeding and raising the feed of 60 to 180 g (preferably about 100 to 140 g, more preferably about 120 g) per a hen once or dividing into two to six times a day and continuously feeding from 10 days to 30 days (at least 26 days) to the hen (feeding and raising process) as the feed for laying hen. From the date past the day on which the ergothioneine content becomes a maximum value (about 26th day after feeding), the mixed amount of the extract solution to the general feed for the hen can be decreased, and it can also prepare so that the maximum may be maintained. It is possible to the egg to the subject of collecting egg if it is the egg which contains the ergothioneine passed more than two days from feeding. But, it is desirable to the egg which the ergothioneine content on not more than 5 days before and after the 26 days from feeding became the maximum or a value near it and stabilized, to the subject of collecting egg. The laying egg has the boiled egg and the fried egg processed. The processed food made of the egg has the mayonnaise, supplement, fish paste, and cosmetics, etc.

The egg laid the laying hen which fed and raised the feed containing the ergothioneine mentioned above laid is containing the ergothioneine. The egg white of the egg and the processed food of the egg white contain the ergothioneine 5 to 13 μg/g. The egg yolk and the processed food of the egg yolk contain the ergothioneine 3 to 13 μg/g. The egg contains the boiled egg and the fried egg processed. The processed food of the egg white has the supplement, fish paste, and cosmetics, etc. in which the egg white as the raw material. The processed food of the egg yolk has the mayonnaise sauce in which the egg yolk as the raw material.

EXAMPLE 1

Figure 2:
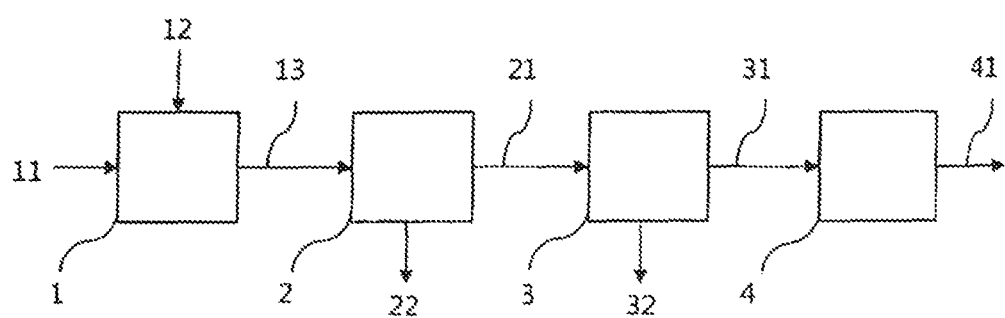
FIG. 2 It is the figure showing the outline of the equipment which manufactures the feed for the laying hen according to the present invention.

The manufacture of the extract solution containing the ergothioneine which is mixed in the general feed for the hen, the manufacture and feeding of the feed of the laying hen were carried out as follows. It describes for this example referring to FIG. 2. In the figure, 1 is a hot water extractor (an alcohol solution extractor), 2 is a compressor, 3 is a thin film concentrator (a brown rice fermentation machine), 4 is a mixing stirrer, 11 is a waste culture medium for Flammulina velutipes, 12 is water, 13 is an extract, 21 is an extract solution containing ergothioneine, 22 is a residue, 31 is a concentrate solution containing ergothioneine, 32 is sejunction water, 41 is a feed of laying hen, respectively. About the alcohol solution extraction and the brown rice fermentation process, it described by the item of the modes for carrying out the invention.

2,200 kg of the waste culture medium for the Flammulina velutipes 11 and 11,000 kg of the water 12 were fed into the hot water extractor 1, the hot water extract was performed at about 97° C. for about 1 hour, and the extract 13 was obtained. The extract 13 was compressed with the compressor 2, 9,200 kg of the extract solution containing the ergothioneine 21 and the residue 22 after separating the extract solution were obtained. The thin film concentrator 3 separated the sejunction water 32 from 9,200 kg of extract solution containing the ergothioneine 21, and 460 kg of the concentrate solution containing the ergothioneine 31 was obtained. Thus, 14 ml of the obtained concentrate solution containing the ergothioneine were mixed in 120 g of the feed for hen used generally, it were mixed with the mixing stirrer 4, and the feed for the laying hen 41 was obtained. The feed for the laying hen 41 of 120 g per a hen was continuously fed to the laying hen for 36 days, dividing into four times a day.

EXAMPLE 2

The feeding and raising to the laying hen, and the measure of the ergothioneine content in the egg white of the egg extracted in the meantime are performed in the following ways. Numbering was carried out to ten hens, respectively, and it stored one hen in the raising gauge, and one egg (a total of ten eggs) which each hen will lay on the 1 day was extracted, numbering was carried out to each egg, and the ergothioneine content in the egg white of each egg was measured. In a fixed amount of the ergothioneine, the chromatogram of an internal standard substance and the ergothioneine are obtained from the egg white which preliminarily added the internal standard substance of the known amount by a high performance chromatography, the amount of the ergothioneine is measured from the ratio of the peak area of the ergothioneine to that of the internal standard substance.

Figure 3:
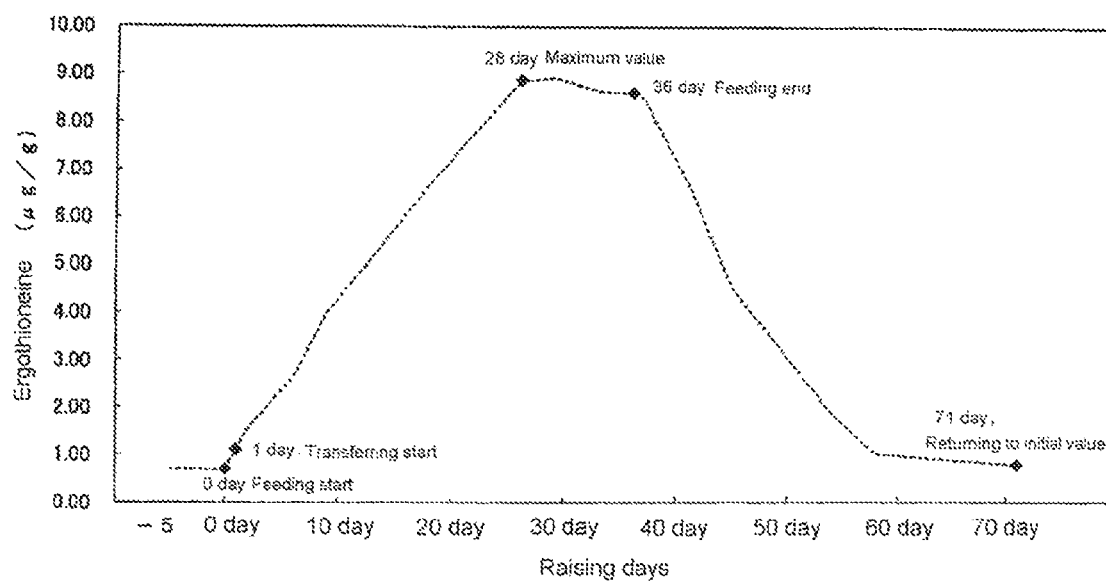
FIG. 3 It is the graph which showed the relation between the feeding and raising days to the laying hen of the feed of the laying hen according to the present invention, and the ergothioneine content in the egg white of the hen's egg.

In the measurement of the ergothioneine content in the egg white, the feed for the hen used generally (the general feed for the hen) was fed for 5 days (minus fifth day to minus first day), the feed of the laying hen which mixed the concentrate solution containing the ergothioneine continuously was fed for 36 days (0 day to 36th day), the feed of the laying hen was stopped after that, the general feed for the hen was started, and it carried out till 71th day. The result is shown in the graph of FIG. 3. In FIG. 3, one egg (a total of ten eggs) which each of the ten hens will lay on the 1 day is extracted for every lapsed days which start of the feed of the general feed for the hen, start of the feed of the laying hen, start of the feed of the general feed for the hen to stop of the feed of the laying hen and continue on the 71th day. The ergothioneine content in each egg white is measured, and the average value of the ergothioneine content in the egg white of these ten eggs is denoted by a graph.

The graph of FIG. 3 shows the following facts. The concentration to the egg white of the ergothioneine of the feed (the feed for the laying hen) of the laying hen which mixed the concentrate solution containing the ergothioneine starts from the first day of the feed start. After the ergothioneine increases linearly, it becomes about 12.8 times as 8.86 μg/g from 0.69 μg/g of initial value (minus fifth day) on 26th day after the feeding start, and the increase in the concentration of the ergothioneine in the egg white stops after that. The feed of the feed of the laying hen was stopped on 36th day after the feeding and raising start of the laying hen after that, when the general feed for the hen was fed, the ergothioneine content decreased. The content of the ergothioneine returned to the value (the initial value) before feed of the feed of the laying hen which mixed the concentrate solution containing the ergothioneine in the 71th day.

EXAMPLE 3

The feeding and raising to the laying hen, and the measurement of the ergothioneine content in the egg yolk of the egg extracted in the meantime are performed in the same way as the example 2. In a fixed amount of the ergothioneine in the measurement of the ergothioneine content in the egg yolk of each egg here, the chromatogram of an internal standard substance and the ergothioneine are obtained from the egg yolk which preliminarily added the internal standard substance of the known amount by a high performance chromatography, the amount of the ergothioneine is measured from the ratio of the peak area of the ergothioneine to that of the internal standard substance.

Figure 4:
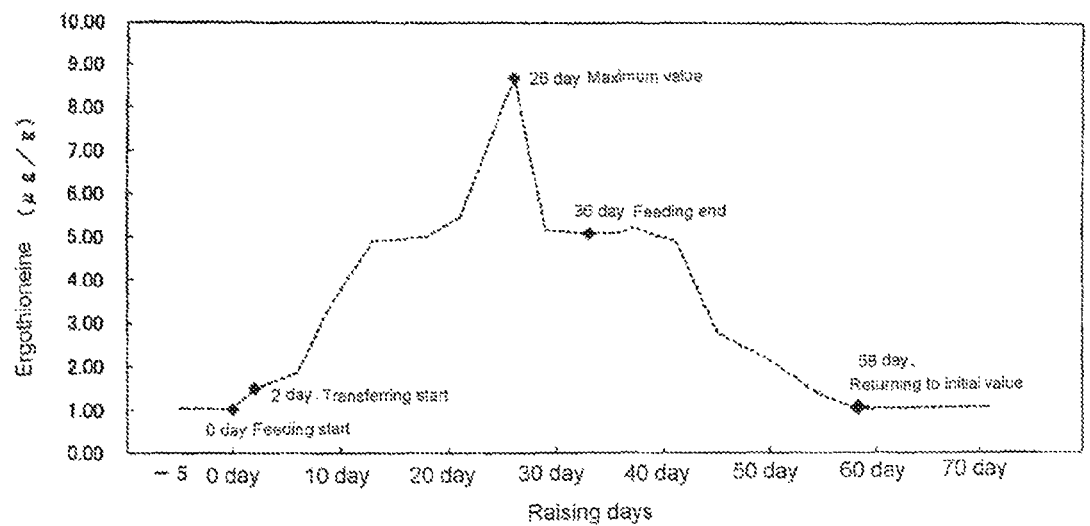
FIG. 4 It is the graph which showed the relation between the feeding and raising days to the laying hen of the feed of the laying hen according to the present invention, and the ergothioneine content in the egg yolk of the hen's egg.

The result of the measurement of the ergothioneine content in the egg yolk is shown in the graph of FIG. 4. In FIG. 4, one egg (a total of ten eggs) which each of the ten hens will lay on the 1 day is extracted for every lapsed days which start of the feed of the general feed for the hen, start of the feed of the laying hen, start of the feed of the general feed for the hen to stop of the feed of the laying hen and continue on the 71th day. The ergothioneine content in each egg yolk is measured, and the average value of the ergothioneine content in the egg yolk of these ten eggs is denoted by a graph.

The graph of FIG. 4 shows the following facts. The concentration to the egg yolk of the ergothioneine of the feed of the laying hen which mixed the concentrate solution containing the ergothioneine starts from the second day of the feed start quickly. It becomes about 8.5 times as 8.7 μg/g from 1.02 μg/g of initial value (minus fifth day) on 26th day after the feeding start, and the increase in the concentration of the ergothioneine in the egg yolk stops after that. The feed of the feed of the laying hen was stopped on 36th day after the feeding start after that, when the feed for the hen used generally (the general feed for the hen) was fed, the ergothioneine content decreased. The content of the ergothioneine returned to the value (the initial value) before feed of the feed of the laying hen in the 58th day.

The ergothioneine incorporated into the inside of the body of the laying hen which fed the feed of the laying hen in the present invention condenses in order of the egg yolk from the egg white so that clearly from the examples 1, 2, and 3, It is accumulated. In the ergothioneine content in the egg white and the egg yolk of the egg which the hen after feeding the feed of the laying hen for a fixed time lays, the progression of the increase stops, and it stabilizes content at high concentration. The egg which contained the ergothioneine in high concentration at this time is obtained.

Table 1 shows the ergothioneine content in the egg white and the egg yolk of the egg in the present invention, a radical scavenging ability value (active oxygen eliminating ability value), and both division value. It analyzes about the relation between the ergothioneine content in the egg white and the egg yolk of the hen's egg in the present invention, and DPPH radical scavenging ability, and the computed result of both division value is shown in Table 1.

TABLE 1

| Item | Egg white | Egg yolk |
|---|---|---|
| Ergothioneine content (E) mAbs | 114.7 | 69.3 |
| Radical scavenging ability (R) mAbs | 155.2 | 55.2 |
| R/E ratio | 1.4 | 0.8 |

The value (R/E ratio) obtained by dividing the DPPH radical scavenging ability value measured with high performance chromatography by the content value of the ergothioneine contained in the hen's egg in the present invention becomes about 1.4 at the egg white and about 0.8 at the egg yolk, so that clearly from Table 1. In the egg laid the hen which fed the feed of the laying hen in the present invention, the ergothioneine in the egg white activates than the ergothioneine in the egg yolk. The ergothioneine in the egg white has much radical scavenging ability rather than the ergothioneine in the egg yolk. The radical scavenging ability per unit weight of the ergothioneine contained in the egg white is 1.4 or more times that of the ergothioneine contained in the egg yolk. Since the active oxygen eliminating ability of the egg white is high, especially the egg white has high antioxidative activity, the white (egg white) of the egg which is generally tend to be shunned becomes a useful part, and it leads to the increase in the demand of the hen's egg as a result.

In the present invention, the extract solution containing the ergothioneine which is obtained by the compression processing the waste culture medium for the edible mushroom from the extract extracted by the alcohol solution or the hot water extracting process, or the condensation solution containing the ergothioneine which obtained by the condensation process of the extract solution is specified quantity mixed to the feed for the hen used generally. The manufactured feed for the laying hen continuously feeds to the hen for prescribed period. It became possible to carry out concentration and accumulation of the ergothioneine into the hen's egg. Especially, the hen's egg having the egg white with high antioxidative activity is producible. Since the waste culture medium used for production of the edible mushroom is used as the raw material, the hen's egg inexpensive having the antioxidative activity is producible. Further, there is the effect that the residue after the hot water extract is recyclable to production of the edible mushroom.

INDUSTRIAL APPLICABILITY

In the present invention, since the feed which uses the extract solution containing the ergothioneine manufactured from the waste culture medium which became unnecessary by using for the production of the edible mushroom is used as the feed of the laying hen, the hen's egg having the high antioxidative activity can produce inexpensive, effective use of the waste culture medium used for production of the edible mushroom which was conventionally troubled by abandonment is enabled. The present invention can expect the contribution to the wide industries, such as the mushroom industry, poultry farming industry, and the manufacturing and selling industry of the feed.

DESCRIPTION OF REFERENCE NUMERALS

1 Hot water extractor (alcohol solution extractor)
2 Compressor
3 Thin film concentrator (brown rice fermentation machine)
4 Mixing stirrer
11 Waste culture medium for Flammulina velutipes
12 Water
13 Extract
21 Extract solution containing ergothioneine
22 Residue
31 Concentrate solution containing ergothioneine
32 Sejunction water
41 Feed for laying hen

What is claimed is:

1. A manufacture method of a feed for a laying hen containing ergothioneine comprising
adding water, hot water, or steam to a waste culture medium used for an edible mushroom production and heating the waste culture medium,
performing a hot water extract for 30 to 90 minutes after reaching 50° C. to 110° C. to obtain an extract,
separating a solid as residue from the extracted extract by a compression processing to obtain an extract solution,
separating and removing moisture from the extract solution to obtain the extract solution containing the ergothioneine which is concentrated to ⅒ to 1/30, and
mixing the extract solution containing the ergothioneine of 4 to 20% by weight ratio to a compound feed.

2. The manufacture method of the feed for the laying hen containing the ergothioneine according to claim 1, wherein the edible mushroom is selected from a Flammulina velutipes, a *Pleurotus eryngii* and a *Lentinula edodes*.

3. A hen's egg comprising an egg white containing ergothioneine 5 to 13 μg/g, and an egg yolk containing ergothioneine 3 to 13 μg/g, and
wherein a radical scavenging ability per unit weight of the ergothioneine contained in the egg white is 1.4 or more times a radical scavenging ability per unit weight of the ergothioneine contained in the egg yolk.

* * * * *

UNITED STATES PATENT AND TRADEMARK OFFICE
CERTIFICATE OF CORRECTION

| | |
|---|---|
| PATENT NO. | : 9,788,567 B2 |
| APPLICATION NO. | : 15/108095 |
| DATED | : October 17, 2017 |
| INVENTOR(S) | : Kazunari Abe et al. |

It is certified that error appears in the above-identified patent and that said Letters Patent is hereby corrected as shown below:

On the Title Page

Item (54), and in the Specification, Column 1, Lines 1-3, replace "ERGOTHIONEINE-CONTAINING HEN¿ S EGG, FEED AND FEEDING AND RAISING METHOD FOR LAYING HEN THAT LAYS ERGOTHIONEINE- CONTAINING HEN¿ S EGG" with
-- ERGOTHIONEINE-CONTAINING HEN'S EGG, FEED AND FEEDING AND RAISING METHOD FOR LAYING HEN THAT LAYS ERGOTHIONEINE- CONTAINING HEN'S EGG --.

Signed and Sealed this
First Day of May, 2018

Andrei Iancu
*Director of the United States Patent and Trademark Office*